(12) United States Patent
Lopez (10) Patent No.: US 10,603,499 B2
(45) Date of Patent: Mar. 31, 2020

(54) TAPERED IMPLANTABLE LEAD AND CONNECTOR INTERFACE AND METHODS OF MAKING AND USING

(71) Applicant: Boston Scientific Neuromodulation Corporation, Valencia, CA (US)

(72) Inventor: Thomas Paul Lopez, Sunland, CA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 123 days.

(21) Appl. No.: 15/944,093

(22) Filed: Apr. 3, 2018

(65) Prior Publication Data
US 2018/0289968 A1    Oct. 11, 2018

Related U.S. Application Data

(60) Provisional application No. 62/483,141, filed on Apr. 7, 2017.

(51) Int. Cl.
| | | |
|---|---|---|
| *A61N 1/375* | (2006.01) | |
| *A61N 1/05* | (2006.01) | |
| *A61N 1/36* | (2006.01) | |

(52) U.S. Cl.
CPC ......... *A61N 1/3752* (2013.01); *A61N 1/0534* (2013.01); *A61N 1/0551* (2013.01); *A61N 1/36071* (2013.01); *H01R 2201/12* (2013.01)

(58) Field of Classification Search
None
See application file for complete search history.

(56) References Cited

U.S. PATENT DOCUMENTS

| | | |
|---|---|---|
| 3,222,471 A | 12/1965 | Steinkamp |
| 3,601,747 A | 8/1971 | Prall et al. |
| 3,718,142 A | 2/1973 | Mulier |
| 3,757,789 A | 9/1973 | Shanker |
| 3,771,106 A | 11/1973 | Matsumoto et al. |
| 3,908,668 A | 9/1975 | Bolduc |
| 3,951,154 A | 4/1976 | Hartlaub |
| 3,990,727 A | 11/1976 | Gallagher |
| 4,003,616 A | 1/1977 | Springer |

(Continued)

FOREIGN PATENT DOCUMENTS

| | | |
|---|---|---|
| EP | 0580928 A1 | 2/1994 |
| EP | 0650694 B1 | 7/1998 |

(Continued)

*Primary Examiner* — Brian T Gedeon
(74) *Attorney, Agent, or Firm* — Lowe Graham Jones PLLC; Bruce E. Black (57) ABSTRACT

An electrical stimulation lead connector includes a connector housing and a plurality of contacts. The connector housing defines a lead lumen having a width, a lead receiving opening, an end stop, a midpoint between the lead receiving opening and the end stop, and a longitudinal length extending from the lead receiving opening to the end stop. The width of the lead lumen decreases from the lead receiving opening to the midpoint and from the midpoint to the end stop. The plurality of contacts is disposed in the connector housing and longitudinally spaced apart from each other along the longitudinal length of the lead lumen. Each of the contacts is configured and arranged to electrically couple to a corresponding terminal of a lead body when an end portion of the lead body is inserted into the lead lumen.

20 Claims, 8 Drawing Sheets

(56) References Cited

U.S. PATENT DOCUMENTS

| | | | |
|---|---|---|---|
| 4,112,953 | A | 9/1978 | Shanker et al. |
| 4,142,532 | A | 3/1979 | Ware |
| 4,180,078 | A | 12/1979 | Anderson |
| 4,245,642 | A | 1/1981 | Skubitz et al. |
| 4,259,962 | A | 4/1981 | Peers-Trevarton |
| 4,310,001 | A | 1/1982 | Comben |
| 4,364,625 | A | 12/1982 | Baker et al. |
| 4,367,907 | A | 1/1983 | Buck |
| 4,411,276 | A | 10/1983 | Dickhudt et al. |
| 4,411,277 | A | 10/1983 | Dickhudt |
| 4,461,194 | A | 7/1984 | Moore |
| 4,466,441 | A | 8/1984 | Skubitz et al. |
| 4,516,820 | A | 5/1985 | Kuzma |
| RE31,990 | E | 9/1985 | Sluetz et al. |
| 4,540,236 | A | 9/1985 | Peers-Trevarton |
| 4,602,624 | A | 7/1986 | Naples et al. |
| 4,603,696 | A | 8/1986 | Cross, Jr. et al. |
| 4,614,395 | A | 9/1986 | Peers-Trevarton |
| 4,630,611 | A | 12/1986 | King |
| 4,695,116 | A | 9/1987 | Bailey et al. |
| 4,695,117 | A | 9/1987 | Kysiak |
| 4,712,557 | A | 12/1987 | Harris |
| 4,715,380 | A | 12/1987 | Harris |
| 4,744,370 | A | 5/1988 | Harris |
| 4,784,141 | A | 11/1988 | Peers-Trevarton |
| 4,832,032 | A | 5/1989 | Schneider |
| 4,840,580 | A | 6/1989 | Saell et al. |
| 4,850,359 | A | 7/1989 | Putz |
| 4,860,750 | A | 8/1989 | Frey et al. |
| 4,867,708 | A | 9/1989 | Iizuka |
| 4,869,255 | A | 9/1989 | Putz |
| 4,898,173 | A | 2/1990 | Daglow et al. |
| 4,899,753 | A | 2/1990 | Inoue et al. |
| 4,951,687 | A | 8/1990 | Ufford et al. |
| 4,995,389 | A | 2/1991 | Harris |
| 5,000,177 | A | 3/1991 | Hoffman et al. |
| 5,000,194 | A | 3/1991 | van den Honert et al. |
| 5,007,435 | A | 4/1991 | Doan et al. |
| 5,007,864 | A | 4/1991 | Stutz, Jr. |
| 5,070,605 | A | 12/1991 | Daglow et al. |
| 5,082,453 | A | 1/1992 | Stutz, Jr. |
| 5,086,773 | A | 2/1992 | Ware |
| 5,135,001 | A | 8/1992 | Sinofsky et al. |
| 5,193,539 | A | 3/1993 | Schulman et al. |
| 5,193,540 | A | 3/1993 | Schulman et al. |
| 5,201,865 | A | 4/1993 | Kuehn |
| 5,241,957 | A | 9/1993 | Camps et al. |
| 5,252,090 | A | 10/1993 | Giurtino et al. |
| 5,261,395 | A | 11/1993 | Oleen et al. |
| 5,312,439 | A | 5/1994 | Loeb |
| 5,324,312 | A | 6/1994 | Stokes et al. |
| 5,330,521 | A | 7/1994 | Cohen |
| 5,336,246 | A | 8/1994 | Dantanarayana |
| 5,348,481 | A | 9/1994 | Ortiz |
| 5,354,326 | A | 10/1994 | Comben et al. |
| 5,358,514 | A | 10/1994 | Schulman et al. |
| 5,368,496 | A | 11/1994 | Ranalletta et al. |
| 5,374,279 | A | 12/1994 | Duffin, Jr. et al. |
| 5,374,285 | A | 12/1994 | Vaiani et al. |
| 5,383,913 | A | 1/1995 | Schiff |
| 5,413,595 | A | 5/1995 | Stutz, Jr. |
| 5,433,734 | A | 7/1995 | Stokes et al. |
| 5,435,731 | A | 7/1995 | Kang |
| 5,458,629 | A | 10/1995 | Baudino et al. |
| 5,486,202 | A | 1/1996 | Bradshaw |
| 5,489,225 | A | 2/1996 | Julian |
| 5,509,928 | A | 4/1996 | Acken |
| 5,522,874 | A | 6/1996 | Gates |
| 5,534,019 | A | 7/1996 | Paspa |
| 5,545,188 | A | 8/1996 | Bradshaw et al. |
| 5,545,189 | A | 8/1996 | Fayram |
| 5,582,180 | A | 8/1996 | Manset et al. |
| 5,560,358 | A | 10/1996 | Arnold et al. |
| 5,679,026 | A | 10/1997 | Fain et al. |
| 5,683,433 | A | 11/1997 | Carson |
| 5,711,316 | A | 1/1998 | Elsberry et al. |
| 5,713,922 | A | 2/1998 | King |
| 5,720,631 | A | 2/1998 | Carson et al. |
| 5,730,628 | A | 3/1998 | Hawkins |
| 5,755,743 | A | 5/1998 | Volz et al. |
| 5,766,042 | A | 6/1998 | Ries et al. |
| 5,782,892 | A | 7/1998 | Castle et al. |
| 5,796,044 | A | 8/1998 | Cobian et al. |
| 5,800,350 | A | 9/1998 | Coppleson et al. |
| 5,800,495 | A | 9/1998 | Machek et al. |
| 5,807,144 | A | 9/1998 | Sivard |
| 5,837,006 | A | 11/1998 | Ocel et al. |
| 5,843,141 | A | 12/1998 | Bischoff et al. |
| 5,843,148 | A | 12/1998 | Gijsbers et al. |
| 5,906,634 | A | 5/1999 | Flynn et al. |
| 5,931,861 | A | 8/1999 | Werner et al. |
| 5,938,688 | A | 8/1999 | Schiff |
| 5,951,595 | A | 9/1999 | Moberg et al. |
| 5,968,082 | A | 10/1999 | Heil |
| 5,987,361 | A | 11/1999 | Mortimer |
| 5,989,077 | A | 11/1999 | Mast et al. |
| 6,006,135 | A | 12/1999 | Kast et al. |
| 6,018,684 | A | 1/2000 | Bartig et al. |
| 6,038,479 | A | 3/2000 | Werner et al. |
| 6,038,481 | A | 3/2000 | Werner et al. |
| 6,042,432 | A | 3/2000 | Hashizawa et al. |
| 6,051,017 | A | 4/2000 | Loeb et al. |
| 6,080,188 | A | 6/2000 | Rowley et al. |
| 6,112,120 | A | 8/2000 | Correas |
| 6,112,121 | A | 8/2000 | Paul et al. |
| 6,125,302 | A | 9/2000 | Kuzma |
| 6,134,478 | A | 10/2000 | Spehr |
| 6,161,047 | A | 10/2000 | King et al. |
| 6,154,678 | A | 11/2000 | Lauro |
| 6,162,101 | A | 12/2000 | Fischer et al. |
| 6,164,284 | A | 12/2000 | Schulman et al. |
| 6,167,311 | A | 12/2000 | Rezai |
| 6,167,314 | A | 12/2000 | Fischer, Sr. et al. |
| 6,175,710 | B1 | 1/2001 | Kamaji et al. |
| 6,181,969 | B1 | 1/2001 | Gord |
| 6,185,452 | B1 | 2/2001 | Schulman et al. |
| 6,192,278 | B1 | 2/2001 | Werner et al. |
| 6,198,969 | B1 | 3/2001 | Kuzma |
| 6,208,894 | B1 | 3/2001 | Schulman et al. |
| 6,224,450 | B1 | 5/2001 | Norton |
| 6,271,094 | B1 | 8/2001 | Boyd et al. |
| 6,295,944 | B1 | 10/2001 | Lovett |
| 6,319,021 | B1 | 11/2001 | Billman |
| 6,321,126 | B1 | 11/2001 | Kuzma |
| 6,322,559 | B1 | 11/2001 | Daulton et al. |
| 6,343,233 | B1 | 1/2002 | Werner et al. |
| 6,364,278 | B1 | 4/2002 | Lin et al. |
| 6,370,434 | B1 | 4/2002 | Zhang et al. |
| 6,391,985 | B1 | 5/2002 | Goode et al. |
| 6,397,108 | B1 | 5/2002 | Camps et al. |
| 6,415,168 | B1 | 7/2002 | Putz |
| 6,428,336 | B1 | 8/2002 | Akerfeldt |
| 6,428,368 | B1 | 8/2002 | Hawkins et al. |
| 6,430,442 | B1 | 8/2002 | Peters et al. |
| 6,466,824 | B1 | 10/2002 | Struble |
| 6,473,654 | B1 | 10/2002 | Chinn |
| 6,498,952 | B2 | 12/2002 | Imani et al. |
| 6,510,347 | B2 | 1/2003 | Borkan |
| 6,516,227 | B1 | 2/2003 | Meadows et al. |
| 6,556,873 | B1 | 4/2003 | Smits |
| 6,564,078 | B1 | 5/2003 | Marino et al. |
| 6,604,283 | B1 | 8/2003 | Kuzma |
| 6,605,094 | B1 | 8/2003 | Mann et al. |
| 6,609,029 | B1 | 8/2003 | Mann et al. |
| 6,609,032 | B1 | 8/2003 | Woods et al. |
| 6,654,641 | B1 | 11/2003 | Froberg |
| 6,662,035 | B2 | 12/2003 | Sochor |
| 6,663,570 | B2 | 12/2003 | Mott |
| 6,671,534 | B2 | 12/2003 | Putz |
| 6,671,553 | B1 | 12/2003 | Helland et al. |
| 6,678,564 | B2 | 1/2004 | Ketterl et al. |
| 6,725,096 | B2 | 4/2004 | Chinn et al. |
| 6,741,892 | B1 | 5/2004 | Meadows et al. |
| 6,757,039 | B2 | 6/2004 | Ma |

(56) References Cited

U.S. PATENT DOCUMENTS

| | | |
|---|---|---|
| 6,757,970 B1 | 7/2004 | Kuzma et al. |
| 6,799,991 B2 | 10/2004 | Williams et al. |
| 6,805,675 B1 | 10/2004 | Gardeski et al. |
| 6,854,994 B2 | 2/2005 | Stein et al. |
| 6,878,013 B1 | 4/2005 | Behan |
| 6,895,276 B2 | 5/2005 | Kast et al. |
| 6,913,478 B2 | 7/2005 | Lamrey |
| 6,921,295 B2 | 7/2005 | Sommer et al. |
| 6,968,235 B2 | 11/2005 | Belden et al. |
| 6,980,863 B2 | 12/2005 | van Venrooj et al. |
| 7,027,852 B2 | 4/2006 | Helland |
| 7,047,084 B2 | 5/2006 | Erickson et al. |
| 7,058,452 B2 | 6/2006 | Dahberg |
| 7,069,081 B2 | 6/2006 | Biggs et al. |
| 7,083,474 B1 | 8/2006 | Fleck et al. |
| 7,108,549 B2 | 9/2006 | Lyu et al. |
| 7,110,827 B2 | 9/2006 | Sage et al. |
| 7,128,600 B2 | 10/2006 | Osypka |
| 7,155,283 B2 | 12/2006 | Ries et al. |
| 7,164,951 B2 | 1/2007 | Ries et al. |
| 7,168,165 B2 | 1/2007 | Calzada et al. |
| 7,191,009 B2 | 3/2007 | Laske et al. |
| 7,195,523 B2 | 3/2007 | Naviaux |
| 7,203,548 B2 | 4/2007 | Whitehurst et al. |
| 7,225,034 B2 | 5/2007 | Ries et al. |
| 7,231,253 B2 | 6/2007 | Tidemand et al. |
| 7,241,180 B1 | 7/2007 | Rentas |
| 7,242,987 B2 | 7/2007 | Holleman et al. |
| 7,244,150 B1 | 7/2007 | Brase et al. |
| 7,270,568 B2 | 9/2007 | Osypka |
| 7,283,878 B2 | 10/2007 | Brostrom et al. |
| 7,286,882 B2 | 10/2007 | Cole |
| 7,287,995 B2 | 10/2007 | Stein et al. |
| 7,292,890 B2 | 11/2007 | Whitehurst et al. |
| 7,396,335 B2 | 7/2008 | Gardeski et al. |
| 7,402,083 B2 | 7/2008 | Kast et al. |
| 7,422,487 B2 | 9/2008 | Osypka |
| 7,430,958 B2 | 10/2008 | Wong |
| 7,437,193 B2 | 10/2008 | Parramon et al. |
| 7,450,997 B1 | 11/2008 | Pianca et al. |
| 7,489,971 B1 | 2/2009 | Franz |
| 7,512,446 B2 | 3/2009 | Honeck |
| 7,516,447 B2 | 4/2009 | Marvin et al. |
| 7,526,339 B2 | 4/2009 | Lahti et al. |
| 7,539,542 B1 | 5/2009 | Malinowski |
| 7,548,788 B2 | 6/2009 | Chinn et al. |
| 7,554,493 B1 | 6/2009 | Rahman |
| 7,583,999 B2 | 9/2009 | Bedenbaugh |
| 7,585,190 B2 | 9/2009 | Osypka |
| 7,590,451 B2 | 9/2009 | Tronnes et al. |
| 7,650,184 B2 | 1/2010 | Walter |
| 7,668,601 B2 | 2/2010 | Hegland et al. |
| 7,672,734 B2 | 3/2010 | Anderson et al. |
| 7,736,191 B2 | 6/2010 | Sochor |
| 7,758,384 B2 | 7/2010 | Alexander et al. |
| 7,761,165 B1 | 7/2010 | He et al. |
| 7,761,985 B2 | 7/2010 | Hegland et al. |
| 7,783,359 B2 | 8/2010 | Meadows |
| 7,792,590 B1 | 9/2010 | Pianca et al. |
| 7,798,864 B2 | 9/2010 | Barker et al. |
| 7,803,021 B1 | 9/2010 | Brase |
| 7,809,446 B2 | 10/2010 | Meadows |
| 7,822,477 B2 | 10/2010 | Rey et al. |
| 7,822,482 B2 | 10/2010 | Gerber |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,949,395 B2 | 5/2011 | Kuzma |
| 7,974,705 B2 | 7/2011 | Zdeblick et al. |
| 7,974,706 B2 | 7/2011 | Moffitt et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,046,073 B1 | 10/2011 | Pianca |
| 8,046,074 B2 | 10/2011 | Barker |
| 8,078,280 B2 | 12/2011 | Sage |
| 8,099,177 B2 | 1/2012 | Dahlberg |
| 8,100,726 B2 | 1/2012 | Harlan et al. |
| 8,140,163 B2 | 3/2012 | Daglow et al. |
| 8,167,660 B2 | 5/2012 | Dilmaghanian et al. |
| 8,175,710 B2 | 5/2012 | He |
| 8,190,259 B1 | 5/2012 | Smith et al. |
| 8,206,180 B1 | 6/2012 | Kast et al. |
| 8,224,450 B2 | 7/2012 | Brase |
| 8,225,504 B2 | 7/2012 | Dye et al. |
| 8,239,042 B2 | 8/2012 | Chinn et al. |
| 8,271,094 B1 | 9/2012 | Moffitt et al. |
| 8,295,944 B2 | 10/2012 | Howard et al. |
| 8,301,255 B2 | 10/2012 | Barker |
| 8,321,025 B2 | 11/2012 | Bedenbaugh |
| 8,342,887 B2 | 1/2013 | Gleason et al. |
| 8,359,107 B2 | 1/2013 | Pianca et al. |
| 8,364,278 B2 | 1/2013 | Pianca et al. |
| 8,391,985 B2 | 3/2013 | McDonald |
| 8,412,330 B2 | 4/2013 | Kast et al. |
| 8,527,054 B2 | 9/2013 | North |
| 8,583,237 B2 | 11/2013 | Bedenbaugh |
| 8,600,507 B2 | 12/2013 | Brase et al. |
| 8,682,439 B2 | 3/2014 | DeRohan et al. |
| 8,688,235 B1 | 4/2014 | Pianca et al. |
| 8,784,143 B2 | 7/2014 | Edgell et al. |
| 8,831,742 B2 | 9/2014 | Pianca et al. |
| 8,849,396 B2 | 9/2014 | DeRohan et al. |
| 8,849,415 B2 | 9/2014 | Bedenbaugh |
| 8,897,876 B2 | 11/2014 | Sundaramurthy et al. |
| 8,897,891 B2 | 11/2014 | Romero |
| 8,968,331 B1 | 3/2015 | Sochor |
| 9,101,775 B2 | 8/2015 | Barker |
| 9,149,630 B2 | 10/2015 | Howard et al. |
| 9,162,048 B2 | 10/2015 | Romero et al. |
| 9,234,591 B2 | 1/2016 | Dilmaghanian et al. |
| 9,270,070 B2 | 2/2016 | Pianca |
| 9,289,596 B2 | 3/2016 | Leven |
| 9,352,147 B2 | 5/2016 | Nguyen-stella et al. |
| 9,381,348 B2 | 7/2016 | Romero et al. |
| 9,403,022 B2 | 8/2016 | Ries et al. |
| 9,409,032 B2 | 8/2016 | Brase et al. |
| 9,440,066 B2 | 9/2016 | Black |
| 9,498,618 B2 | 11/2016 | Stetson et al. |
| 9,498,620 B2 | 11/2016 | Romero et al. |
| 9,504,839 B2 | 11/2016 | Leven |
| 9,604,068 B2 | 3/2017 | Malinowski |
| 9,656,093 B2 | 5/2017 | Villarta et al. |
| 9,770,598 B2 | 9/2017 | Malinowski et al. |
| 9,855,413 B2 | 1/2018 | Vadlamudi et al. |
| 2001/0023368 A1 | 9/2001 | Black et al. |
| 2002/0143376 A1 | 10/2002 | Chinn et al. |
| 2002/0156513 A1 | 10/2002 | Borkan |
| 2002/0183817 A1 | 12/2002 | Van Venrooij et al. |
| 2003/0163171 A1 | 8/2003 | Kast et al. |
| 2004/0064164 A1 | 4/2004 | Ries et al. |
| 2004/0230268 A1 | 11/2004 | Huff et al. |
| 2004/0260373 A1 | 12/2004 | Ries et al. |
| 2005/0015130 A1 | 1/2005 | Gill |
| 2005/0027326 A1 | 2/2005 | Ries et al. |
| 2005/0027327 A1 | 2/2005 | Ries et al. |
| 2005/0038489 A1 | 2/2005 | Grill |
| 2005/0043770 A1 | 2/2005 | Hine et al. |
| 2005/0043771 A1 | 2/2005 | Sommer et al. |
| 2005/0137665 A1 | 6/2005 | Cole |
| 2005/0171587 A1 | 8/2005 | Daglow et al. |
| 2005/0186829 A1 | 8/2005 | Balsells |
| 2005/0272280 A1 | 12/2005 | Osypka |
| 2006/0015163 A1 | 1/2006 | Brown |
| 2006/0025841 A1 | 2/2006 | McIntyre |
| 2006/0030918 A1 | 2/2006 | Chinn |
| 2006/0167522 A1 | 7/2006 | Malinowski |
| 2006/0224208 A1 | 10/2006 | Naviaux |
| 2006/0247697 A1 | 11/2006 | Sharma et al. |
| 2006/0247749 A1 | 11/2006 | Colvin |
| 2006/0259106 A1 | 11/2006 | Arnholt et al. |

(56) References Cited

U.S. PATENT DOCUMENTS

| | | |
|---|---|---|
| 2007/0042648 A1 | 2/2007 | Balsells |
| 2007/0142889 A1 | 6/2007 | Whitehurst et al. |
| 2007/0150036 A1 | 6/2007 | Anderson |
| 2007/0161294 A1 | 7/2007 | Brase et al. |
| 2007/0168007 A1 | 7/2007 | Kuzma et al. |
| 2007/0203546 A1 | 8/2007 | Stone et al. |
| 2007/0219551 A1 | 9/2007 | Honour et al. |
| 2008/0077186 A1 | 3/2008 | Thompson et al. |
| 2008/0103580 A1 | 5/2008 | Gerber |
| 2008/0114230 A1 | 5/2008 | Addis |
| 2008/0139031 A1 | 6/2008 | Ries et al. |
| 2008/0177167 A1 | 7/2008 | Janzig et al. |
| 2008/0208277 A1 | 8/2008 | Janzig et al. |
| 2008/0208278 A1 | 8/2008 | Janzig et al. |
| 2008/0208279 A1 | 8/2008 | Janzig et al. |
| 2008/0215125 A1 | 9/2008 | Farah et al. |
| 2008/0255647 A1 | 10/2008 | Jensen et al. |
| 2008/0274651 A1 | 11/2008 | Boyd et al. |
| 2009/0054941 A1 | 2/2009 | Eggen et al. |
| 2009/0187222 A1 | 7/2009 | Barker |
| 2009/0204192 A1 | 8/2009 | Carlton et al. |
| 2009/0264943 A1 | 10/2009 | Barker |
| 2009/0276021 A1 | 11/2009 | Meadows et al. |
| 2009/0287191 A1 | 11/2009 | Ferren et al. |
| 2010/0029127 A1 | 2/2010 | Sjostedt |
| 2010/0030298 A1 | 2/2010 | Martens et al. |
| 2010/0036468 A1 | 2/2010 | Decre et al. |
| 2010/0057176 A1 | 3/2010 | Barker |
| 2010/0070012 A1 | 3/2010 | Chinn et al. |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0268298 A1 | 10/2010 | Moffift et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0004267 A1 | 1/2011 | Meadows |
| 2011/0005069 A1 | 1/2011 | Pianca |
| 2011/0022100 A1 | 1/2011 | Brase et al. |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0184480 A1 | 7/2011 | Kast et al. |
| 2011/0238129 A1 | 9/2011 | Moffitt et al. |
| 2011/0245903 A1 | 10/2011 | Schulte et al. |
| 2011/0270330 A1 | 11/2011 | Janzig et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0053646 A1 | 3/2012 | Brase et al. |
| 2012/0071937 A1 | 3/2012 | Sundaramurthy et al. |
| 2012/0071949 A1 | 3/2012 | Pianca et al. |
| 2012/0165911 A1 | 6/2012 | Pianca |
| 2012/0185019 A1 | 7/2012 | Schramm et al. |
| 2012/0197375 A1 | 8/2012 | Pianca et al. |
| 2012/0203302 A1 | 8/2012 | Moffit et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0232603 A1 | 9/2012 | Sage |
| 2012/0253443 A1 | 10/2012 | Dilmaghanian et al. |
| 2012/0259386 A1 | 10/2012 | DeRohan et al. |
| 2012/0316615 A1 | 12/2012 | DiGiore et al. |
| 2013/0053864 A1 | 2/2013 | Geroy et al. |
| 2013/0098678 A1 | 4/2013 | Barker |
| 2013/0105071 A1 | 5/2013 | DiGiore et al. |
| 2013/0109254 A1 | 5/2013 | Klardie et al. |
| 2013/0116754 A1 | 5/2013 | Sharma et al. |
| 2013/0149031 A1 | 6/2013 | Changsrivong et al. |
| 2013/0197424 A1 | 8/2013 | Bedenbaugh |
| 2013/0197602 A1 | 8/2013 | Pianca et al. |
| 2013/0197603 A1 | 8/2013 | Eiger |
| 2013/0218154 A1 | 8/2013 | Carbunaru |
| 2013/0261684 A1 | 10/2013 | Howard |
| 2013/0288501 A1 | 10/2013 | Russell et al. |
| 2013/0304140 A1 | 11/2013 | Derohan et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0088666 A1 | 3/2014 | Goetz et al. |
| 2014/0142671 A1 | 5/2014 | Moffitt et al. |
| 2014/0148885 A1 | 5/2014 | DeRohan et al. |
| 2014/0180375 A1 | 6/2014 | Pianca et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0025609 A1 | 1/2015 | Govea |
| 2015/0045864 A1 | 2/2015 | Howard |
| 2015/0066120 A1 | 3/2015 | Govea |
| 2015/0119965 A1 | 4/2015 | Govea |
| 2015/0151113 A1 | 6/2015 | Govea et al. |
| 2015/0209575 A1 | 7/2015 | Black |
| 2015/0360023 A1 | 12/2015 | Howard et al. |
| 2015/0374978 A1 | 12/2015 | Howard et al. |
| 2016/0059019 A1 | 3/2016 | Malinowski et al. |
| 2016/0129242 A1 | 5/2016 | Malinowski |
| 2016/0129265 A1 | 5/2016 | Malinowski |
| 2016/0158558 A1 | 6/2016 | Shanahan et al. |
| 2016/0206891 A1 | 7/2016 | Howard et al. |
| 2016/0228692 A1 | 8/2016 | Steinke et al. |
| 2016/0296745 A1 | 10/2016 | Govea et al. |
| 2016/0375238 A1 | 12/2016 | Leven et al. |
| 2017/0072187 A1 | 3/2017 | Howard et al. |
| 2017/0143978 A1 | 5/2017 | Barker |
| 2017/0203104 A1 | 7/2017 | Nageri et al. |
| 2017/0361108 A1 | 12/2017 | Leven |
| 2018/0008832 A1 | 1/2018 | Leven |
| 2018/0028820 A1 | 2/2018 | Nageri |
| 2018/0093098 A1 | 4/2018 | Nageri et al. |
| 2018/0214687 A1 | 8/2018 | Nageri et al. |
| 2018/0243570 A1 | 8/2018 | Malinowski et al. |
| 2018/0289968 A1 | 10/2018 | Lopez |
| 2018/0369596 A1 | 12/2018 | Funderburk |
| 2019/0030345 A1 | 1/2019 | Funderburk |
| 2019/0083793 A1 | 3/2019 | Nageri |
| 2019/0083794 A1 | 3/2019 | Nageri |
| 2019/0103696 A1 | 4/2019 | Conger |

FOREIGN PATENT DOCUMENTS

| | | |
|---|---|---|
| EP | 0832667 B1 | 2/2004 |
| EP | 1181947 B1 | 1/2006 |
| EP | 1625875 | 2/2006 |
| EP | 2092952 A1 | 8/2009 |
| WO | 1997032628 A1 | 9/1997 |
| WO | 1999055411 A3 | 2/2000 |
| WO | 2000038574 A1 | 7/2000 |
| WO | 2001058520 A1 | 8/2001 |
| WO | 2002068042 A1 | 9/2002 |
| WO | 2004045707 A1 | 6/2004 |
| WO | 2008018067 A2 | 2/2008 |
| WO | 2008053789 A1 | 5/2008 |
| WO | 2008100841 | 8/2008 |
| WO | 2009025816 A1 | 2/2009 |
| WO | 2009102536 A1 | 8/2009 |
| WO | 2009/148939 | 12/2009 |
| WO | 2013162775 A2 | 10/2013 |
| WO | 2014018092 A1 | 1/2014 |

TAPERED IMPLANTABLE LEAD AND CONNECTOR INTERFACE AND METHODS OF MAKING AND USING

CROSS-REFERENCE TO RELATED APPLICATIONS

This application claims the benefit under 35 U.S.C. § 119(e) of U.S. Provisional Patent Application Ser. No. 62/483,141, filed Apr. 7, 2017, which is incorporated herein by reference.

FIELD

The present invention is directed to the area of implantable electrical stimulation systems and methods of making and using the systems, and in particular connectors for stimulation leads and methods of making and using the connectors.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), at least one lead, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a connector that includes an electrical stimulation lead connector that includes a connector housing. The connector housing defines a lead lumen having a width, a lead receiving opening, an end stop, a midpoint between the lead receiving opening and the end stop, and a longitudinal length extending from the lead receiving opening to the end stop. The width of the lead lumen decreases from the lead receiving opening to the midpoint and from the midpoint to the end stop. The electrical stimulation lead connector also includes a plurality of contacts disposed in the connector housing and longitudinally spaced apart from each other along the longitudinal length of the lead lumen. Each of the contacts is configured and arranged to electrically couple to a corresponding terminal of a lead body when an end portion of the lead body is inserted into the lead lumen.

In at least some embodiments, the width of the lead lumen decreases monotonically from the lead receiving opening to the midpoint and from the midpoint to the end stop. In at least some embodiments, the lead lumen has an outer surface with a slope having a grade of at least 0.5%. In at least some embodiments, the width of the lead lumen continuously tapers along the longitudinal length of the lead lumen from the lead receiving opening to the end stop. In at least some embodiments, the width of the lead lumen decreases uniformly along the longitudinal length of the lead lumen from the lead receiving opening to the end stop.

In at least some embodiments, the width of the lead lumen decreases in discrete steps along the longitudinal length of the lead lumen from the lead receiving opening to the end stop. In at least some embodiments, the width of the lead lumen decreases incrementally along the longitudinal length of the lead lumen from the lead receiving opening to the end stop.

In at least some embodiments, each of the contacts defines a portion of the lead lumen. In at least some embodiments, each of the contacts has an inner diameter that is different than an inner diameter of at least another one of the contacts. In at least some embodiments, at least one of the contacts has an inner diameter that tapers from a larger inner diameter at one end of the at least one contact to smaller inner diameter at another end of the at least one contact. In at least some embodiments, a first one of the contacts has an inner diameter that exceeds an inner diameter of a second one of the contacts, where the first one of the contacts is nearer the lead receiving opening than the second one of the contacts. In at least some embodiments, the contact nearest the end stop has an inner diameter that is smaller than an inner diameter of each of the other contacts.

Another embodiment is an electrical stimulation lead connector system that includes any of the electrical stimulation lead connectors described above and an electrical stimulation lead. The electrical stimulation lead includes a lead body comprising a longitudinal surface, a distal end portion, a proximal end portion, a proximal tip, and a longitudinal length. The proximal end portion is configured and arranged for insertion into the electrical stimulation lead connector and has a non-uniform width that increases from the proximal tip. The electrical stimulation lead also includes a plurality of terminals disposed along the proximal end portion of the lead body. Each of the terminals is configured and arranged to electrically couple to a corresponding one of the contacts of the electrical stimulation lead connector when the proximal end portion of the lead body is inserted into the lead lumen of the connector housing of the electrical stimulation lead connector. The electrical stimulation lead additionally includes a plurality of electrodes disposed along the distal end portion of the lead body. The electrical stimulation lead further includes a plurality of conductors electrically coupling the terminals to the electrodes.

In at least some embodiments, the width of the proximal end portion of the lead body has a grade of at least 0.5%. In at least some embodiments, the width of the proximal end portion of the lead body continuously tapers toward the proximal tip. In at least some embodiments, the width of the proximal end portion of the lead body increases uniformly from the proximal tip. In at least some embodiments, each of the terminals that is distal to a most proximal one of the terminals has a width that exceeds a width of the most proximal one of the terminals.

A further embodiment is an electrical stimulation lead that includes a lead body. The lead body includes a longitudinal surface, a distal end portion, a proximal end portion, a proximal tip, and a longitudinal length. The proximal end portion is configured and arranged for insertion into an electrical stimulation lead connector and has a non-uniform width that increases from the proximal tip. The lead also includes a plurality of terminals disposed along the proximal end portion of the lead body. Each of the terminals is configured and arranged to electrically couple to a corresponding one of a plurality of contacts of the electrical stimulation lead connector when the proximal end portion of the lead body is inserted into a lead lumen of a connector housing of the electrical stimulation lead connector. The lead additionally includes a plurality of electrodes disposed along the distal end portion of the lead body. The lead further includes a plurality of conductors electrically coupling the terminals to the electrodes.

In at least some embodiments, the width of the proximal end portion of the lead body has a grade of at least 0.5%. In at least some embodiments, the width of the proximal end portion of the lead body continuously tapers toward the proximal tip. In at least some embodiments, the width of the proximal end portion of the lead body increases uniformly from the proximal tip.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems, and in particular connectors for latching stimulation leads and methods of making and using the connectors.

Suitable implantable electrical stimulation systems include, but are not limited to, a least one lead with at least one electrode disposed along a distal end of the lead and at least one terminal disposed along the at least one proximal end of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference.

Figure 1:
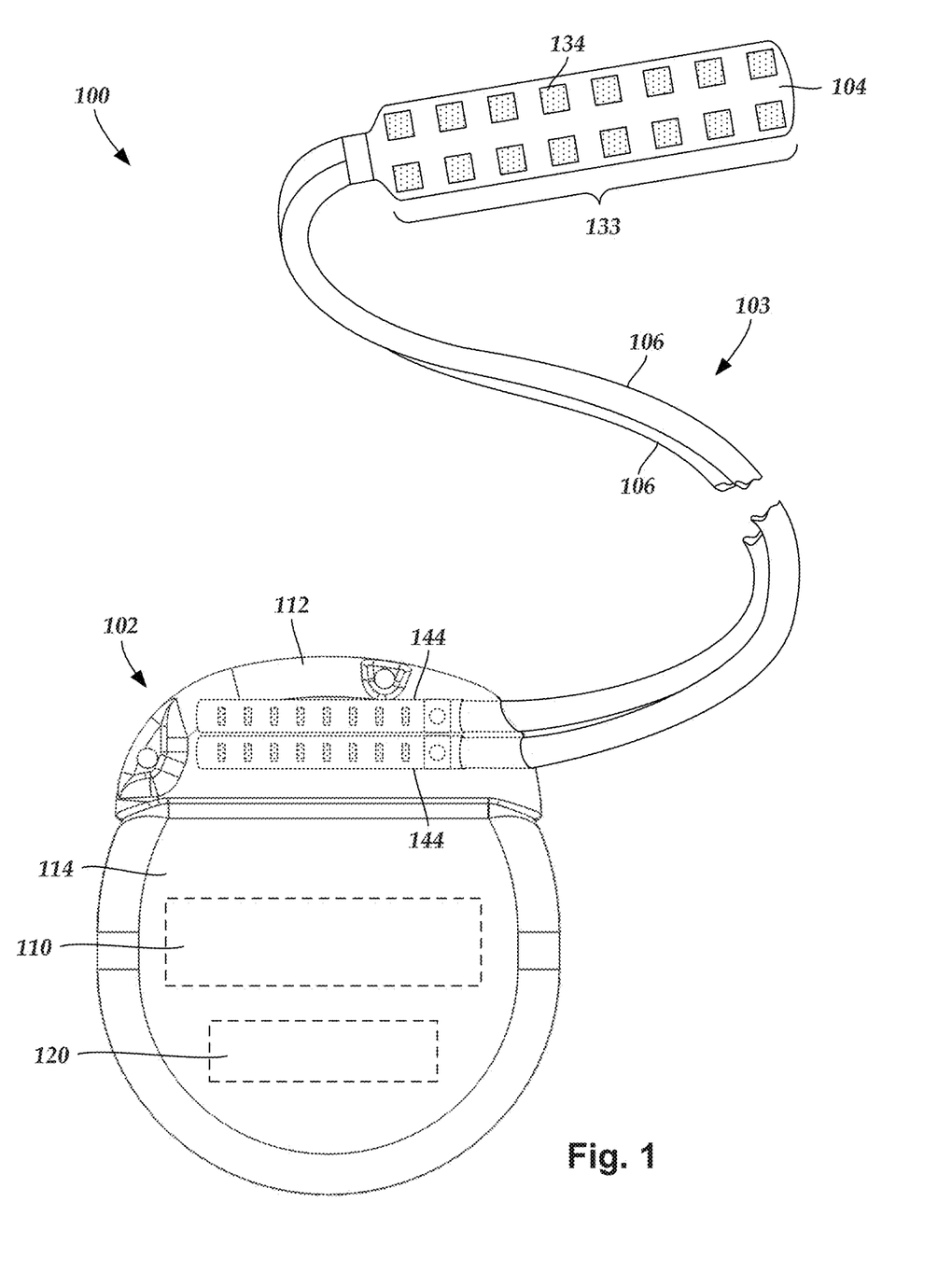
FIG. 1 is a schematic side view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (for example, a stimulator or pulse generator) 102 and a lead 103 coupleable to the control module 102. The lead 103 includes a paddle body 104 and at least one lead body 106. In FIG. 1, the lead 103 is shown having two lead bodies 106. It will be understood that the lead 103 can include any suitable number of lead bodies including, for example, one, two, three, four, five, six, seven, eight or more lead bodies 106. An array 133 of electrodes, such as electrode 134, is disposed on the paddle body 104, and an array of terminals (for example, 310 in FIG. 3A) is disposed along each of the at least one lead body 106. In at least some embodiments, there may be a single electrode 134 or a single terminal.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
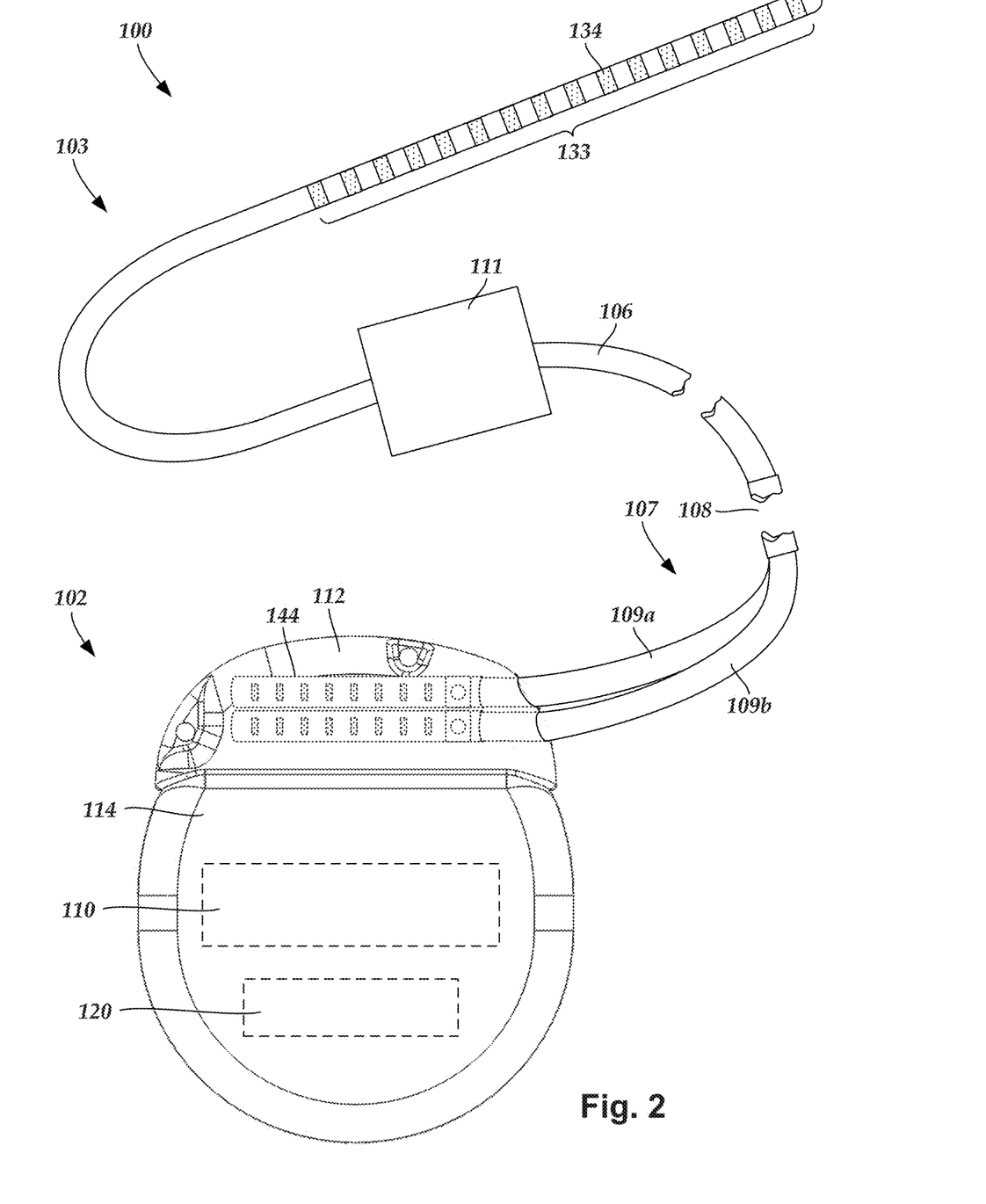
FIG. 2 is a schematic side view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the at least one lead body 106. In at least some embodiments, the lead 103 is isodiametric along a longitudinal length of the lead body 106. FIG. 2 also illustrates a lead anchor 111 disposed around a portion of the lead 103 to anchor the lead to surrounding tissue. The lead anchor 111 has a connector with a lead lumen that receives a portion of the lead and a fastener to attach the lead anchor to the lead.

The lead 103 can be coupled to the control module 102 in any suitable manner. In FIG. 1, the lead 103 is shown coupling directly to the control module 102. In at least some other embodiments, the lead 103 couples to the control module 102 via at least one intermediate device (324 in FIG. 3B). For example, in at least some embodiments at least one lead extension 324 (see, for example, FIG. 3B) can be disposed between the lead 103 and the control module 102 to extend the distance between the lead 103 and the control module 102. Other intermediate devices may be used in addition to, or in lieu of, at least one lead extension including, for example, a splitter, an adaptor, or the like or combinations thereof. It will be understood that, in the case where the electrical stimulation system 100 includes multiple intermediate devices disposed between the lead 103 and the control module 102, the intermediate devices may be configured into any suitable arrangement.

In FIG. 2, the electrical stimulation system 100 is shown having a splitter 107 configured for facilitating coupling of the lead 103 to the control module 102. The splitter 107 includes a splitter connector 108 configured to couple to a proximal end of the lead 103, and at least one splitter tail 109*a* and 109*b* configured to couple to the control module 102 (or another splitter, a lead extension, an adaptor, or the like).

With reference to FIGS. 1 and 2, the control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured to make an electrical connection between the lead 103 and the electronic subassembly 110 of the control module 102.

The electrical stimulation system 100 or components of the electrical stimulation system 100, including the paddle body 104, the at least one of the lead bodies 106, and the control module 102, are typically implanted into the body of a patient. The electrical stimulation system 100 can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, at least one of the electrodes 134 are formed from at least one of: platinum, platinum iridium, palladium, palladium rhodium, or titanium.

Any suitable number of electrodes 134 can be disposed on the lead 103 including, for example, one, two, three, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes 134 of the paddle body 104 (or at least one lead body 106) are typically disposed in, or separated by, a non-conductive, biocompatible material such as, for example, silicone, polyurethane, polyetheretherketone ("PEEK"), epoxy, and the like or combinations thereof. The at least one lead body 106 and, if applicable, the paddle body 104 may be formed in the desired shape by any process including, for example, molding (including injection molding), casting, and the like. The non-conductive material typically extends from the distal ends of the at least one lead body 106 to the proximal end of each of the at least one lead body 106.

In the case of paddle leads, the non-conductive material typically extends from the paddle body 104 to the proximal end of each of the at least one lead body 106. Additionally, the non-conductive, biocompatible material of the paddle body 104 and the at least one lead body 106 may be the same or different. Moreover, the paddle body 104 and the at least one lead body 106 may be a unitary structure or can be formed as two separate structures that are permanently or detachably coupled together.

Figure 3A:
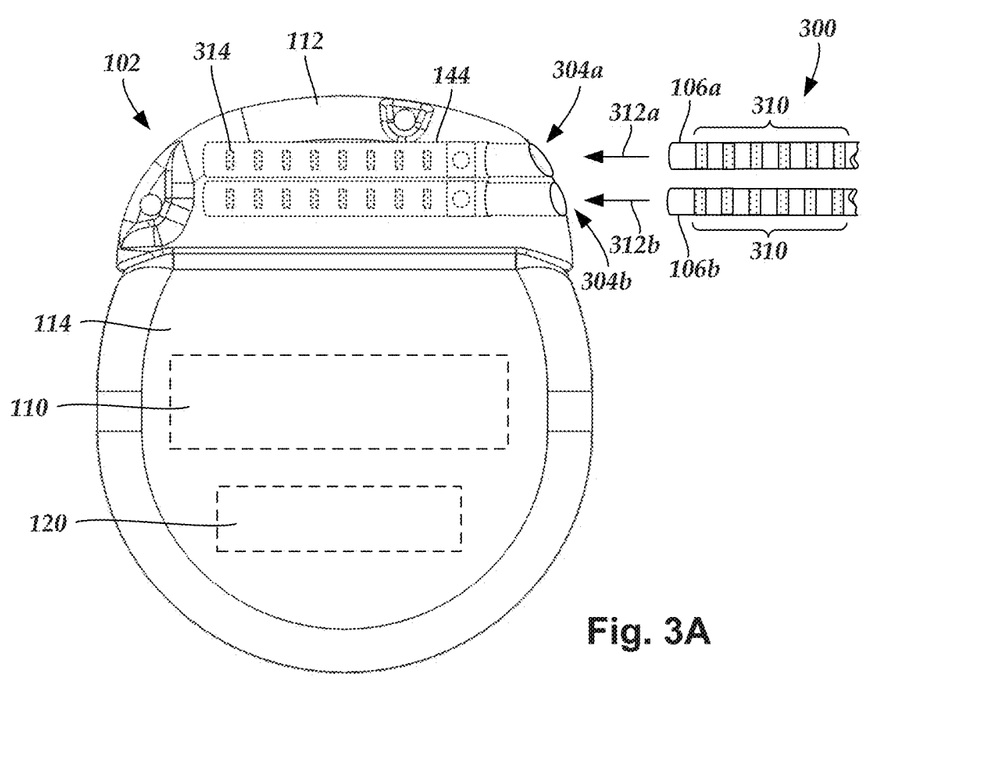
FIG. 3A is a schematic side view of one embodiment of the control module of FIG. 1 configured to electrically couple to a lead body, according to the invention.

Terminals (for example, 310 in FIG. 3A) are typically disposed along the proximal end of the at least one lead body 106 of the electrical stimulation system 100 (as well as any splitters, lead extensions, adaptors, or the like) for electrical connection to corresponding connector contacts (for example, 314 in FIG. 3A). The connector contacts are disposed in connectors (for example, 144 in FIGS. 1-3B; and 322 in FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, at least one electrode 134 are electrically coupled to each terminal. In at least some embodiments, each terminal is only connected to one electrode 134.

FIG. 3A is a schematic side view of one embodiment of a proximal end of at least one elongated device 300 configured for coupling to one embodiment of the control module connector 144. The at least one elongated device 300 may include, for example, at least one of the lead bodies 106 of FIG. 1, at least one intermediate device (for example, a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312*a* and 312*b*. In FIG. 3A (and in other figures), the connector housing 112 is shown having two ports 304*a* and 304*b*. The connector housing 112 can define any suitable number of ports including, for example, one, two, three, four, five, six, seven, eight, or more ports. Each port is an opening to a lead lumen within which a portion of the lead can be inserted.

The control module connector 144 also includes a plurality of connector contacts, such as connector contact 314, disposed within the lead lumen associated with each port 304*a* and 304*b*. When the elongated device 300 is inserted into the ports 304*a* and 304*b*, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

Figure 3B:
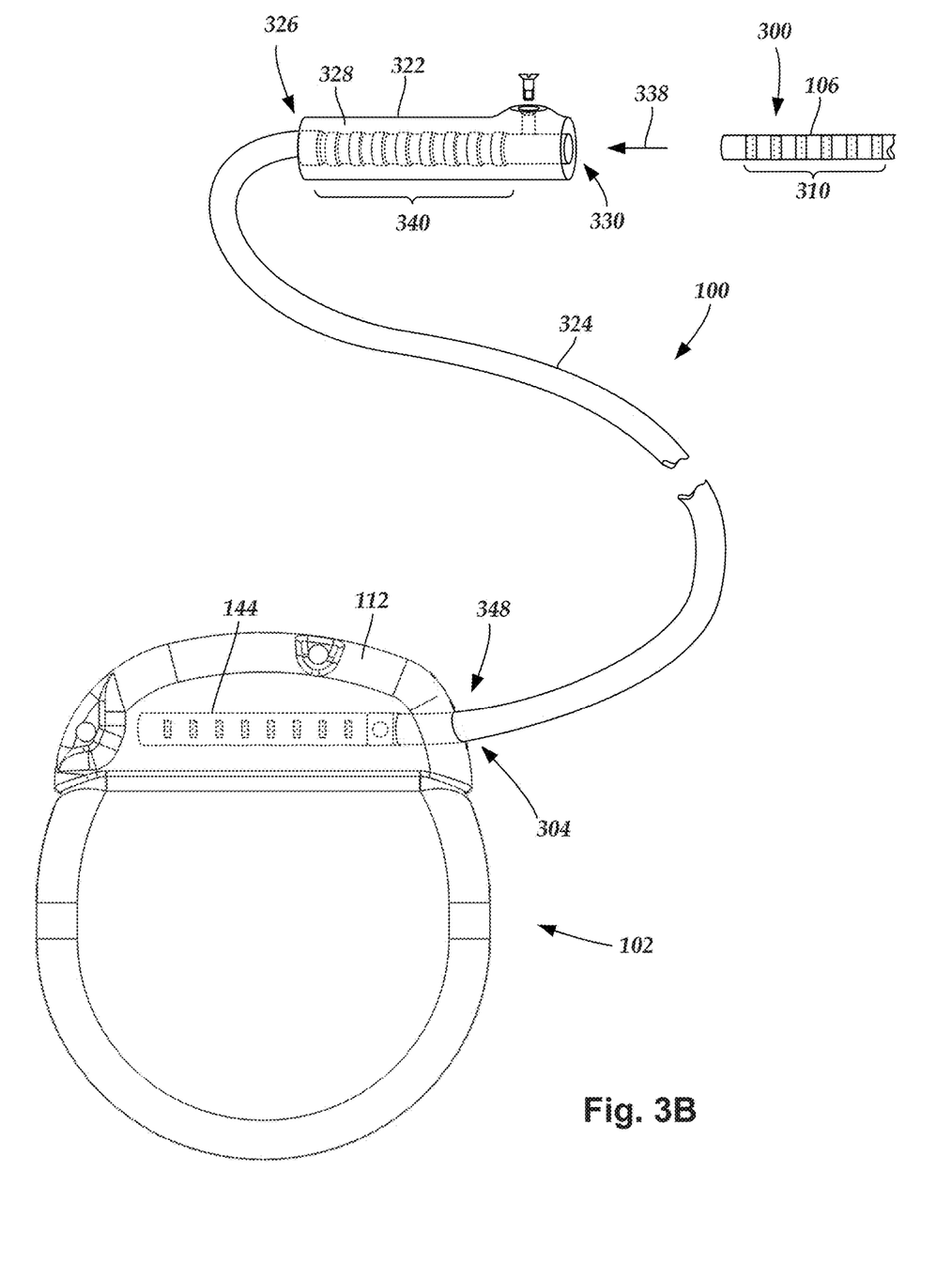
FIG. 3B is a schematic side view of one embodiment of a lead extension configured to electrically couple a lead body to a control module, according to the invention.

FIG. 3B is a schematic side view of another embodiment of the electrical stimulation system 100. The electrical stimulation system 100 includes a lead extension 324 that is configured to couple at least one elongated device 300 (for example, one of the lead bodies 106 of FIGS. 1 and 2, the splitter 107 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured to couple to a single elongated device 300. In alternate embodiments, the lead extension 324 is configured to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 and associated lead lumen into which terminals 310 of the elongated device 300 can be inserted, as shown by directional arrow 338. The connector housing 328 also includes a plurality of connector contacts, such as connector contacts 340. When the elongated device 300 is inserted into the port 330 and its associated lead lumen, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured for insertion into a connector disposed in another lead extension (or another intermediate device). In other embodiments (and as shown in FIG. 3B), the proximal end 348 of the lead extension 324 is configured for insertion into the control module connector 144.

The terms "proximal" and "distal" are used consistently with respect to all elements of the lead and system and are defined relative to the proximal end portion of the lead which attaches to the control module. The distal end portion of the lead has the electrodes disposed thereon.

Figures 4A, 4B, 4C, 4D:
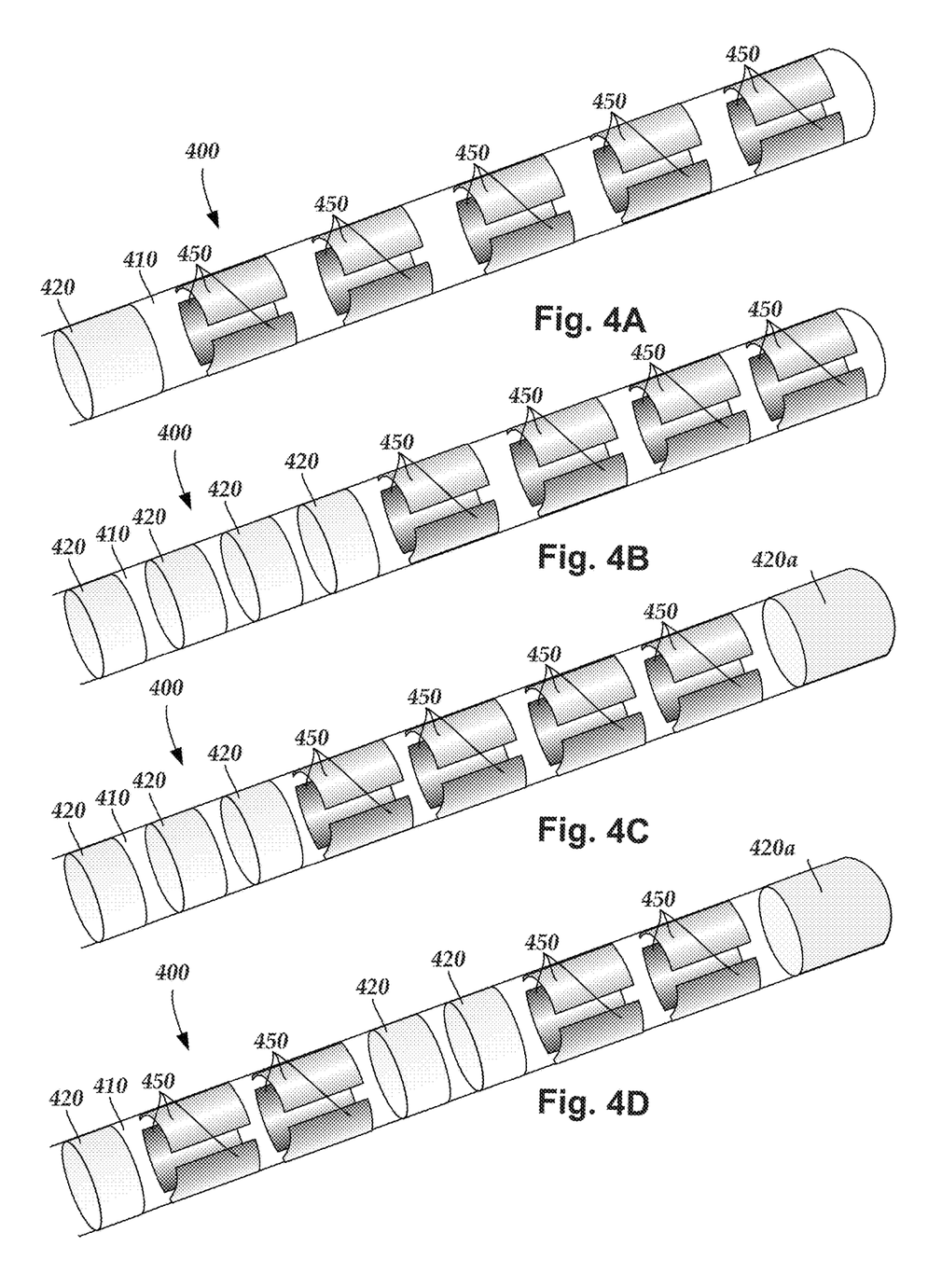
FIG. 4A is a schematic perspective view of one embodiment of a distal end of a lead containing a ring electrode and segmented electrodes, according to the invention.
FIG. 4B is a schematic perspective view of a second embodiment of a distal end of a lead containing ring and segmented electrodes, according to the invention.
FIG. 4C is a schematic perspective view of a third embodiment of a distal end of a lead containing ring and segmented electrodes, according to the invention.
FIG. 4D is a schematic perspective view of a fourth embodiment of a distal end of a lead containing ring and segmented electrodes, according to the invention.

FIGS. 4A and 4B illustrate leads 400 with segmented electrodes 450, ring electrodes 420, and a lead body 410. While FIGS. 4A and 4B show the sets of segmented electrodes 450 as each including three segmented electrodes, the sets of segmented electrodes 450 can include any number of segmented electrodes 450, such as two, four, five, six, or more segmented electrodes. The sets of segmented electrodes 450 can be aligned with each other or staggered.

When the lead 400 includes both ring electrodes 420 and segmented electrodes 450, the ring electrodes 420 and the segmented electrodes 450 may be arranged in any suitable configuration. For example, when the lead 400 includes ring electrodes 420 and segmented electrodes 450, the ring electrodes 420 can flank some or all of the segmented electrodes 450 (see, for example, FIGS. 4C and 4D). Alternately, the ring electrodes 420 can be disposed proximal to the sets of segmented electrodes 450 (see, for example, FIGS. 4A and 4B), or the sets of ring electrodes 420 can be disposed distal to the sets of segmented electrodes 450 (not shown). One of the ring electrodes 420 can be a tip electrode (420a in FIGS. 4C and 4D). It will be understood that other configurations are possible as well (for example, alternating ring and segmented electrodes, or the like).

By varying the selection of the segmented electrodes 450, different coverage of the target neurons may be selected. For example, the electrode arrangement of FIGS. 4A and 4B may be useful if the physician anticipates that the neural target will be closer to a distal tip of the lead body 410, while arranging the ring electrodes 420 to be distal to the segmented electrodes 450 (not shown) may be useful if the physician anticipates that the neural target will be closer to a proximal end of the lead body 410.

Any combination of ring electrodes 420 and segmented electrodes 450 may be disposed on the lead 400. For example, the lead may include a first ring electrode 420, two sets of segmented electrodes 450; each set formed of four segmented electrodes 450, and a final ring electrode 420 at the end of the lead (not shown). This configuration may simply be referred to as a 1-4-4-1 configuration. It may be useful to refer to the electrodes with this shorthand notation. Thus, the embodiment of FIG. 4A may be referred to as a 1-3-3-3-3-3 configuration, while the embodiment of FIG. 4B may be referred to as a 1-1-1-1-3-3-3-3 configuration. The embodiments of FIGS. 4C and 4D include tip electrodes 420a. FIG. 4C shows a 1-1-1-3-3-3-3-1 configuration while FIG. 4D shows a 1-3-3-1-1-3-3-1 configuration. Accordingly, segmented ring electrodes may be separated from each other by segmented electrodes, and segmented electrodes may be separated from each other by ring electrodes.

Other electrode configurations include, for example, a 1-3-3-1 configuration (where two sets of segmented electrodes, each having three segmented electrodes, are disposed on the lead), a 1-1-4-4 configuration (where two sets of segmented electrodes, each having four segmented electrodes, are disposed on the lead), a 4-4-1-1 configuration (where two sets of segmented electrodes, each having four segmented electrodes, are disposed on the lead), a 2-2-2-2 configuration (where four sets of segmented electrodes are disposed on the lead), and a 4-4 configuration (where two sets of segmented electrodes, each having four segmented electrodes 550 are disposed on the lead). In some embodiments, the lead includes 16 electrodes. Possible configurations for a 16-electrode lead include, but are not limited to, 4-4-4-4; 1-1-6-8; 5-3-3-3-3-1 (and all rearrangements of this configuration); and 2-2-2-2-2-2-2-2. Any other suitable segmented electrode arrangements (with or without ring electrodes) can be used including, but not limited to, those disclosed in U.S. Provisional Patent Application Ser. No. 62/113,291 and U.S. Patent Applications Publication Nos. 2012/0197375 and 2015/0045864, all of which are incorporated herein by reference in their entirety. In at least some embodiments, a lead includes a terminal for each electrode on the lead (for example, a lead with 16 electrodes may include 16 terminals).

The amount of force to insert the proximal end of a lead into a connector or to remove the proximal end of the lead from the connector (or duration or quantity of application of that force) typically increases with each additional terminal on the lead. For example, each contact (or other component in the connector) that a terminal passes during insertion into or removal from the connector can interfere with insertion or removal. In this example, when multiple contacts (or other components in the connector) interfere with multiple terminals at once, the amount of force applied to progressively insert or remove the lead can increase. Also in this example, as the number of interfering contacts (or other components in the connector) that a terminal must pass increases, the duration or quantity of application of force applied to insert or remove the lead can increase. Although a segmented electrode lead (e.g., a directional lead) is used as an example herein, these considerations, as well as the arrangements and structure described below, can apply to any type of lead including, but not limited to, paddle leads (see, for example, FIG. 1) or leads with only ring electrodes (see, for example, FIG. 2) or the like.

Consequently, a lead that includes a large number of terminals along a single tail of the lead may prove difficult for a physician to insert into or remove from a connector (at least in comparison to a lead that includes fewer terminals). To mitigate this issue, a lead that includes 16 terminals may have the tail split into two tails, each having 8 terminals (see, for example, FIGS. 1 and 2). This configuration, however, requires two connectors (one for each proximal tail), thereby increasing the size of the connector housing that is implanted in the patient.

Although some of the embodiments described below are presented as connectors of control modules, it will be understood that the arrangements described below can also be applied to other connectors, such as connectors for lead extensions (seem for example, FIG. 3B), splitters, adapters, anchors, or the like.

Also, although some of the embodiments described below are presented as connectors to receive the proximal end of leads, it will be understood that the arrangements described below can also be applied to a connector that receives any end of a lead extension or other elongate member having terminals, contacts, or the like. In general, any elongate member can have first contacts (for example, electrodes for a lead or conductive contacts for a lead extension) disposed along a distal portion of the elongate member and second contacts (for example, segmented terminals) disposed along a proximal portion of the elongate member.

Figure 5A:
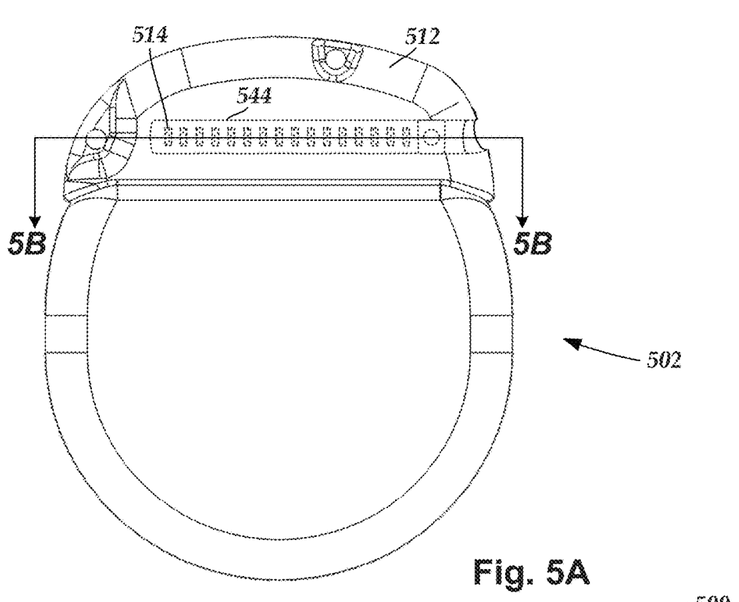
FIG. 5A is a schematic side view of another embodiment of a control module configured to electrically couple to a lead body, according to the invention.
Figure 5B:
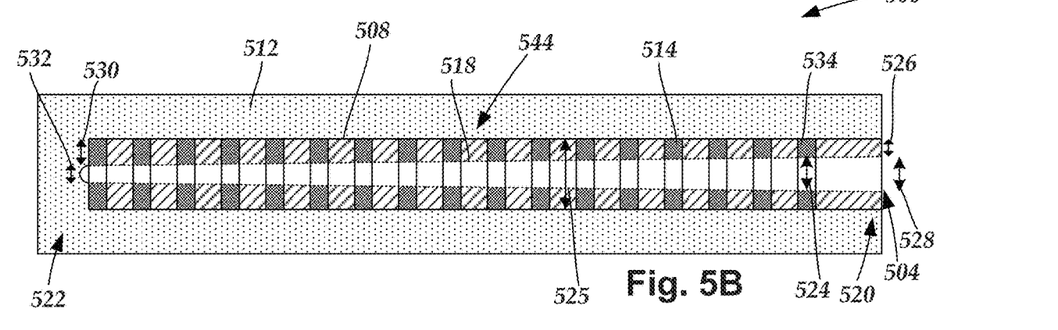
FIG. 5B is a schematic longitudinal cross-sectional view of one embodiment of a connector of the control module of FIG. 5A taken at line 5B-5B, according to the invention.
Figure 5C:
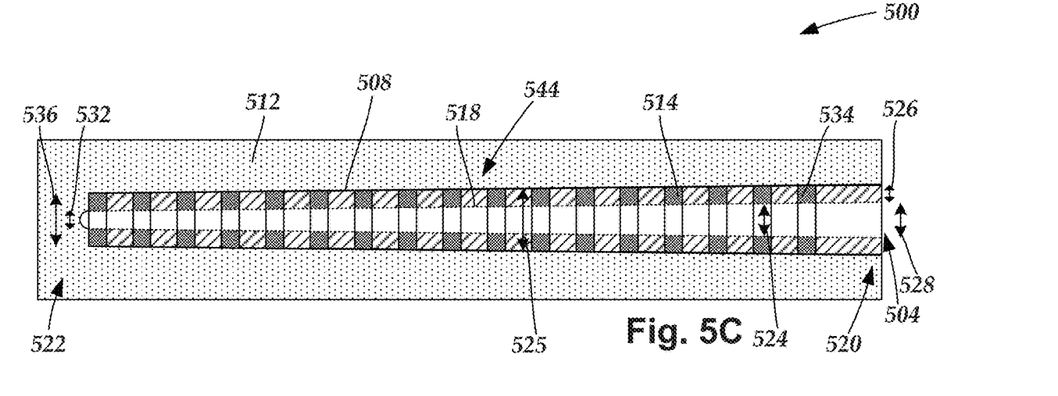
FIG. 5C is a schematic longitudinal cross-sectional view of another embodiment of a connector of the control module of FIG. 5A taken at line 5B-5B, according to the invention.
Figure 5D:
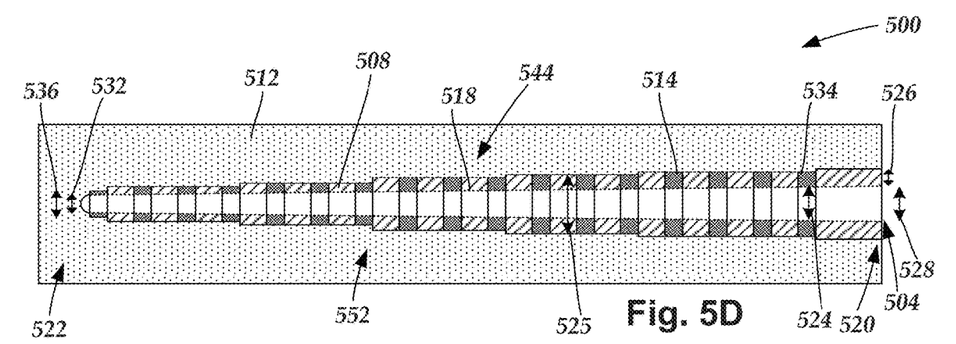
FIG. 5D is a schematic longitudinal cross-sectional view of a further embodiment of a connector of the control module of FIG. 5A taken at line 5B-5B, according to the invention.
Figure 5E:
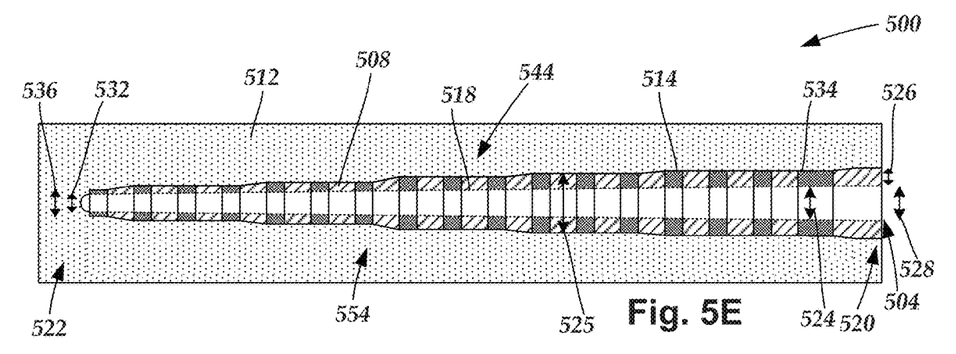
FIG. 5E is a schematic longitudinal cross-sectional view of yet another embodiment of a connector of the control module of FIG. 5A taken at line 5B-5B, according to the invention.

FIG. 5A is a schematic side view of one embodiment of a control module 502 having a connector housing 512 that includes a connector 544 with connector contacts 514. FIG. 5B is a schematic longitudinal cross-sectional view of one embodiment of the connector 544 taken at line 5B-5B. Other embodiments of the connector 544 are illustrated in FIGS. 5C to 5E. The connector housing 512 defines a port 504. In other embodiments, the connector housing 512 defines, two, three, four, five, six, seven, eight, or more ports. Each port is an opening to a lead lumen 518. Each port is associated with a plurality of connector elements that, at least in part, define the lead lumen 518. While the illustrated lead lumen 518 is closed at the proximal end, other embodiments include a lead lumen that is open at both the distal and proximal ends. The connector elements may include, for example, connector contacts 514, spacers 508, retention blocks 534, seals, strain relief, or the like. Any other suitable connector elements can be used including, but not limited to, those disclosed in U.S. Provisional Patent Application Ser. Nos. 62/044,050 and 61/473,574, U.S. Patent Applications Publication No. 2016/0059019, and U.S. Pat. No. 8,682,439, all of which are incorporated herein by reference in their entirety.

The lead lumen has a distal width 528 at the lead receiving opening 520 of the lead lumen 518. The connector elements that define the lead lumen 518 may have different radial thicknesses 526 or inner diameters 524 along the longitudinal length of the lead lumen 518. For example, the radial thicknesses can range from a distal radial thickness 526 for the distal-most connector element down to a proximal radial thickness 530 for the proximal-most connector element.

The lead lumen 518 has a width that varies along the longitudinal length of the lead lumen 518. For example, in the embodiments illustrated in FIGS. 5B to 5E, the width of the lead lumen 518 continuously tapers along the longitudinal length of the lead lumen 518 from the distal width 528 down to the proximal width 532. In these embodiments, the width of the lead lumen 518 decreases monotonically and uniformly. For example, the width of the lead lumen 518 may have a continuous slope (for example, a slope that has at least a 0.5%, 0.75%, 1%, 1.25%, 1.5%, 2%, or 3% grade). In other embodiments, the width of the lead lumen 518 may decrease incrementally or non-uniformly.

The outer diameter 525 or radial thickness 526 of the contact elements may be uniform or vary along the length of the connector. For example, in the embodiment illustrated in FIG. 5B, the outer diameters 525 of the contact elements remain the same and the radial thicknesses 526 increase along the longitudinal length of the connector to the proximal radial thickness 530. In the embodiment illustrated in FIG. 5C, the outer diameters 525 of the contact elements decrease while the radial thicknesses 526 remain constant. In the embodiment illustrated in FIG. 5D, the outer diameters 525 of the contact elements decrease incrementally in discrete steps 552 along the longitudinal length of the lead lumen 518. In at least some embodiments, there are one, two, three, four, five, six, seven, eight, or more connector elements for each discrete step 552. There may be one, two, three, four, six, eight, sixteen, or more (or any other number of) discrete steps 552.

In the embodiment illustrated in FIG. 5E, the outer diameters 525 of the contact elements are constant over various sections of the longitudinal length of the lead lumen 518 and changes in discrete slopes 554 that extend along other sections of the longitudinal length. In at least some embodiments, the slopes 554 span one, two, three, four, five, six, seven, eight, or more connector elements. In at least some embodiments, the discrete slopes 554 are defined by connector contacts 514, spacers 508, retention blocks 534, seals, strain reliefs, or the like that each have outer diameters 525 that vary from their distal end portions to their proximal end portions. In at least some embodiments, the connector includes at least one discrete step 552 and at least one discrete slope 554.

In at least some embodiments, the lead lumen 518 has an end stop 522, with a proximal width 532, and a lead receiving opening 520, with a distal width 528 that exceeds the proximal width 532. In at least some embodiments, the varying width of the lead lumen 518 facilitates inserting a greater portion of the insertion portion 550 of the lead body 506 into the lead lumen 518 prior to encountering substantial resistance to insertion (at least in comparison to a lead lumen and an insertion portion that have constant widths). In at least some embodiments, the distal width 528 of the lead lumen 518 is at least 20%, 25%, 30%, 35%, 40%, 45%, 50%, 55%, 60%, 65%, 70%, 75%, 80%, 85%, 90%, 95%, or 100% greater than the proximal width 532 of the lead lumen 518.

In at least some embodiments, at least one connector element has an inner diameter 524 that exceeds the inner diameter of the adjacent connector element that is distal to the at least one connector element. For example, every other connector element along the longitudinal length of the lead lumen 518 may be a spacer 508 that separates two connector contacts 514. In this example, the inner diameter of the spacer 508 may be greater than the inner diameter of the one of the connector contacts 514 that the spacer 508 separates and less than the inner diameter of the other of the connector contacts. Also in this example, the distal-most connector contact 514 of a pair of connector contacts 514 has an inner diameter that exceeds the inner diameter of the proximal-most connector contact 514 of the pair of connector contacts 514. In at least some embodiments, the inner diameter of a connector element is defined as the smallest inner diameter of that connector element.

The connector elements can be disposed in the connector in any suitable manner including, for example, an interference fit, adhesive, welding, soldering, or the like. The connector contacts 514 can be formed from any electrically-conductive material suitable for implantation including, for example, one or more shape-memory materials, MP35N, stainless steel, or the like. In at least some embodiments, a connector contact 514 includes a contact housing and at least one contact contained in the contact housing. In at least some embodiments, the contact housing and the at least one contact are both formed from electrically-conductive materials and can be electrically coupled to each other. In at least some embodiments, each connector element can be a single-piece assembly. For example, a contact housing and a connector contact 514 or a spacer 508 contained in the contact housing can be collectively formed from the same, single piece of material.

In at least some embodiments, the spacers 508 can facilitate correctly spacing the contacts 514 to align with terminals on an inserted lead body. In at least some embodiments, the spacers 508 can also perform as or include seals. In at least some embodiments, the spacers 508 are made of non-conductive, biocompatible material suitable for implantation.

In at least some embodiments, the outer cross-sectional shape of the connector elements is circular, substantially circular, polygonal, substantially polygonal, or the like while defining a tubular passage through the connector element that forms a portion of the lead lumen 518. In at least some embodiments, the lead lumen 518 may form any circumferential shape suitable for receiving a proximal end portion of a lead body. In at least some embodiments, the cross-sectional shape of the lead lumen 518 is circular, substantially circular, polygonal, substantially polygonal, or the like. For example, the lead lumen 518 and corresponding lead can have a polygonal cross-sectional shape, such as a rectangular, hexagonal, or octagonal cross-sectional shape. In such instances, the width 528 corresponds to a distance between two opposing sides of the rectangular, hexagonal, octagonal, or other polygonal cross-sectional shape. For these cross-sectional shapes, two or more widths 528 are defined for a lead lumen 518 and corresponding lead 506 and, in some instances, for example, for some rectangular cross-sectional shapes, the two or more widths 528 differ in size. In some embodiments, the lead lumen 518 and corresponding lead 506 may decrease along only one of those widths. In other embodiments, the lead lumen 518 and corresponding lead 506 may decrease along two or more (or all) of those widths. The connector contacts 514 and spacers 508 are described herein as being cylindrical, but it will be understood that they can also have a substantially circular, polygonal, or substantially polygonal cross-sectional shape. For such cross-sectional shapes, the inner and outer dimensions of the connector contacts 514 and spacers 508 may vary in the same manner as described above for the inner diameter 524 and outer diameter 525 of the connector contacts 514 or the width 528 of the lead lumen 518.

In at least some embodiments, the connector elements that define the lead lumen 518 include at least one, two, three, four, six, eight, ten, 12, 14, or 16 connector contacts 514; zero, one, two, three, four, six, eight, ten, 12, 14, 16, or more spacers 508; and zero, one, or more retention blocks 534. In at least some embodiments, the connector contacts 514 each have the same or different longitudinal length as other connector contacts 514. In at least some embodiments, the spacers 508 each have the same or different longitudinal length as other spacers 508. In at least some embodiments, the retention block 534 has the same or different longitudinal length as at least one connector contact 514. In at least some embodiments, the number of spacers is equal to, or one more than, the number of connector contacts. In at least some embodiments, the number of spacers is equal to, or one more than, the combined number of connector contacts and retention blocks.

In at least some embodiments, some of the connector elements are resilient or include resilient portions. Examples of resilient connector elements can include resilient contacts, coiled springs, leaf springs, seals, or the like that form at least part of a connector contact 514. In at least some embodiments, the inner diameter (or the radial thickness) of a resilient connector element can be defined as the inner diameter (or the radial thickness) either a) when the resilient connector element is compressed (for example, when the lead body 506 of FIG. 5F is inserted into the lead lumen 518) or b) when the resilient member is not compressed (for example, when the lead body 506 of FIG. 5F is removed from the lead lumen 518).

Any suitable type of connector contact can be used including, but not limited to, those described in U.S. Pat. Nos. 6,741,892; 7,244,150; and 8,682,439; U.S. Patent Application Publications Nos. 2008/0071320; 2011/0022100; and 2016/0059019; and U.S. Patent Application Ser. No. 62/193,472, all of which are incorporated herein by reference. In at least some embodiments, at least one of the connector contacts 514 may include a connector-contact assembly. In at least some embodiments, connector-contact assemblies include contact housings that contain at least one portion of one or more resilient members. In at least some embodiments, a contact housing forms a cylindrical shape, having an outer surface about the exterior portion of the cylindrical shape and an inner surface that defines a portion of the lead lumen 518 that extends through the cylindrical shape.

Figure 5F:
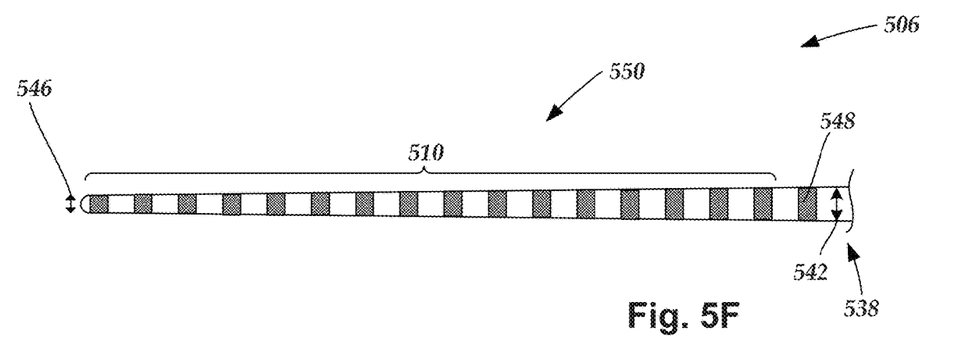
FIG. 5F is a schematic side view of one embodiment of a proximal end portion of a lead configured to electrically couple to the control module of FIG. 5A, according to the invention.

FIG. 5F is a schematic side view of one embodiment of an insertion portion 550 (e.g., proximal end portion) of a lead 506 configured to electrically couple to the control module 502 of FIG. 5A. In at least some embodiments, the insertion portion 550 has a width that varies along the longitudinal length of the insertion portion 550. For example, the insertion portion 550 has a proximal width 546 and a distal width 542 that exceeds the proximal width 546. In at least some embodiments, the width of the insertion portion 550 continuously tapers along the longitudinal length of the insertion portion 550 from the distal width 542 down to the proximal width 546 (for example, with a taper that has at least a 0.5%, 0.75%, 1%, 1.25%, 1.5%, 2%, or 3% grade). In other embodiments, the width of the insertion portion 550 decreases in discrete steps or discrete slopes along the longitudinal length of the insertion portion 550. In at least some embodiments, sections with constant widths, discrete steps, or discrete slopes may span across at least one, two, three, four, five, six, seven, eight, or more terminals 510. In at least some embodiments, each portion of the outer surface of the insertion portion 550 is parallel to a corresponding portion of the outer surface of the lead lumen 518.

The insertion portion 550 of the lead body 506 includes a plurality of terminals 510 or other contacts. In at least some embodiments, at least one terminal forms at least one portion of a ring that has a constant width along the longitudinal length of the terminal. In at least some embodiments, at least one terminal forms at least one portion of a ring that has a larger width at the distal end portion of the terminal and a smaller width at the proximal end portion of the terminal. In at least some embodiments, at least one terminal has a width that exceeds a width of the next-most proximal terminal. In at least some embodiments, when the insertion portion 550 is inserted into the lead lumen 518, each terminal aligns with and electrically couples to a corresponding contact in the lead lumen 518. In at least some embodiments, the plurality of terminals 510 includes two, three, four, five, six, seven, eight, nine, ten, 11, 12, 13, 14, 15, or 16 or more terminals.

In at least some embodiments, the insertion portion 550 includes at least one retention sleeve 548. In at least some embodiments, when the insertion portion 550 is inserted into the lead lumen 518, the retention block 534 can be used to facilitate retention of the lead body 506. For example, the retention sleeve 548 may enable applying a fastener (for example, a set screw, pin, or the like) to the retention sleeve 548 through the retention block 534. In at least some embodiments, the retention sleeve 548 can also be a terminal and the retention block 534 can also be a connector contact.

Figure 6:
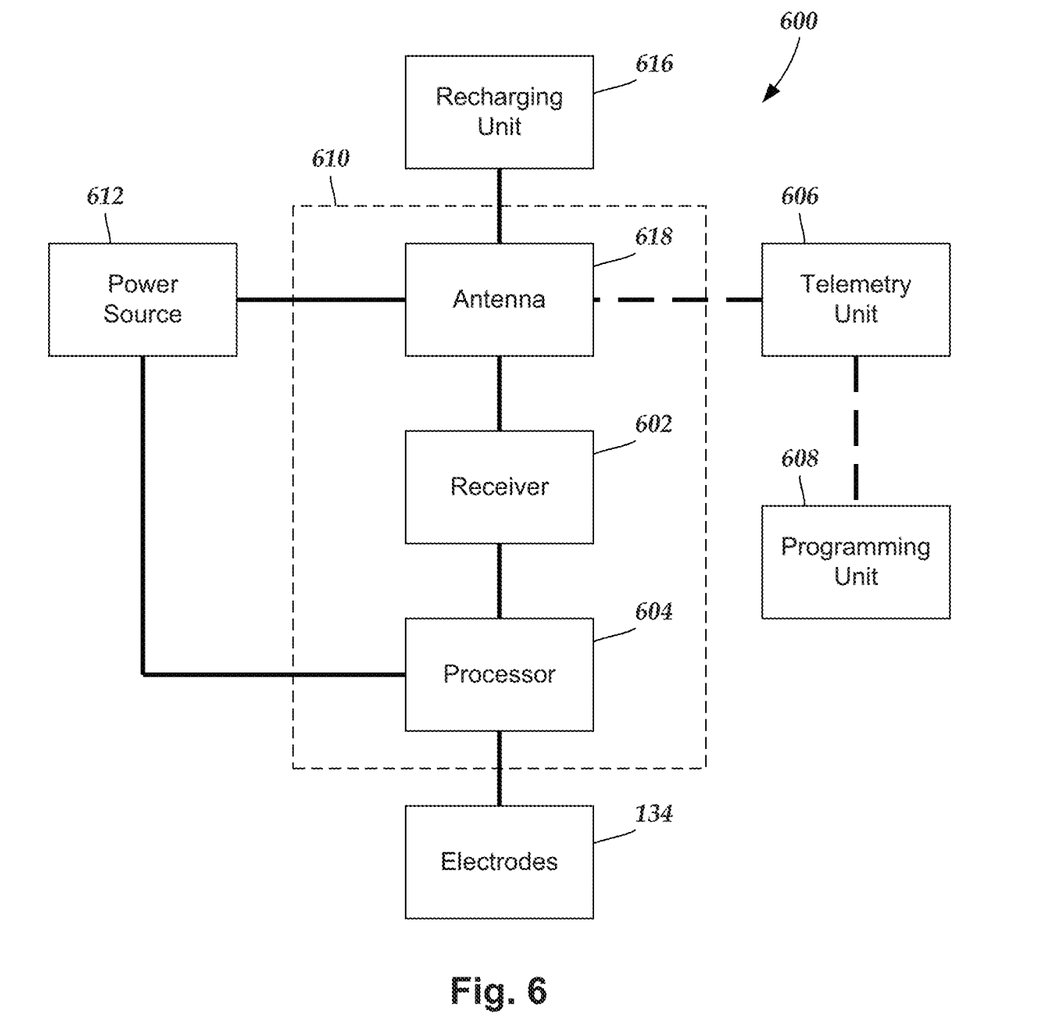
FIG. 6 is a schematic overview of one embodiment of components of a stimulation system, including an electronic subassembly disposed within a control module, according to the invention.

FIG. 6 is a schematic overview of one embodiment of components of an electrical stimulation system 600 including an electronic subassembly 610 disposed within a control module. It will be understood that the electrical stimulation system can include more, fewer, or different components and can have a variety of different configurations including those configurations disclosed in the stimulator references cited herein.

Some of the components (for example, a power source 612, an antenna 618, a receiver 602, and a processor 604) of the electrical stimulation system can be positioned on at least one circuit board or similar carrier within a sealed housing of an implantable pulse generator, if desired. Any power source 612 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, or in addition, power can be supplied by an external power source through inductive coupling via the optional antenna 618 or a secondary antenna. The external power source can be in a device that is mounted on the skin of the user or in a unit that is provided near the user on a permanent or periodic basis.

If the power source 612 is a rechargeable battery, the battery may be recharged using the optional antenna 618, if desired. Power can be provided to the battery for recharging by inductively coupling the battery through the antenna to a recharging unit 916 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 604 is generally included to control the timing and electrical characteristics of the electrical stimulation system. For example, the processor 604 can, if desired, control at least one of the timing, frequency, strength, duration, and waveform of the pulses. In addition, the processor 604 can select which electrodes can be used to provide stimulation, if desired. In at least some embodiments, the processor 604 selects which electrode(s) are cathodes and which electrode(s) are anodes. In at least some embodiments, the processor 604 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 608 that, for example, allows modification of pulse characteristics. In the illustrated embodiment, the processor 604 is coupled to a receiver 602 which, in turn, is coupled to the optional antenna 618. This allows the processor 604 to receive instructions from an external source to, for example, direct the pulse characteristics and the selection of electrodes, if desired.

In one embodiment, the antenna 618 is capable of receiving signals (for example, RF signals) from an external telemetry unit 606 which is programmed by the programming unit 608. The programming unit 608 can be external to, or part of, the telemetry unit 606. The telemetry unit 606 can be a device that is worn on the skin of the user or can be carried by the user and can have a form similar to a pager, cellular phone, or remote control, if desired. As another alternative, the telemetry unit 606 may not be worn or carried by the user but may only be available at a home station or at a clinician's office. The programming unit 608 can be any unit that can provide information to the telemetry unit 606 for transmission to the electrical stimulation system 600. The programming unit 608 can be part of the telemetry unit 606 or can provide signals or information to the telemetry unit 606 via a wireless or wired connection. One example of a suitable programming unit is a computer operated by the user or clinician to send signals to the telemetry unit 606.

The signals sent to the processor 604 via the antenna 618 and the receiver 602 can be used to modify or otherwise direct the operation of the electrical stimulation system. For example, the signals may be used to modify the pulses of the electrical stimulation system such as modifying at least one of pulse duration, pulse frequency, pulse waveform, and pulse strength. The signals may also direct the electrical stimulation system 600 to cease operation, to start operation, to start charging the battery, or to stop charging the battery. In other embodiments, the stimulation system does not include the antenna 618 or receiver 602 and the processor 604 operates as programmed.

Optionally, the electrical stimulation system 600 may include a transmitter (not shown) coupled to the processor 604 and the antenna 618 for transmitting signals back to the telemetry unit 606 or another unit capable of receiving the signals. For example, the electrical stimulation system 600 may transmit signals indicating whether the electrical stimulation system 600 is operating properly or not or indicating when the battery needs to be charged or the level of charge remaining in the battery. The processor 604 may also be capable of transmitting information about the pulse characteristics so that a user or clinician can determine or verify the characteristics.

The above specification provides a description of the invention and the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation system, comprising:
an electrical stimulation lead connector comprising
a connector housing defining a lead lumen having a width, a lead receiving opening, an end stop, a midpoint between the lead receiving opening and the end stop, and a longitudinal length extending from the lead receiving opening to the end stop, wherein the width of the lead lumen decreases from the lead receiving opening to the midpoint and from the midpoint to the end stop, and
a plurality of contacts disposed in the connector housing and longitudinally spaced apart from each other along the longitudinal length of the lead lumen, wherein each of the contacts is configured and arranged to electrically couple to a corresponding terminal of a lead body when an end portion of the lead body is inserted into the lead lumen; and
an electrical stimulation lead comprising
a lead body comprising a longitudinal surface, a distal end portion, a proximal end portion, a proximal tip, and a longitudinal length, wherein the proximal end portion is configured and arranged for insertion into the electrical stimulation lead connector and has a non-uniform width that monotonically increases from the proximal tip,
a plurality of terminals disposed along the proximal end portion of the lead body, wherein each of the terminals is configured and arranged to electrically couple to a corresponding one of the contacts of the electrical stimulation lead connector when the proximal end portion of the lead body is inserted into the lead lumen of the connector housing of the electrical stimulation lead connector, and
a plurality of electrodes disposed along the distal end portion of the lead body; and
a plurality of conductors electrically coupling the terminals to the electrodes.

2. The electrical stimulation system of claim 1, wherein the width of the lead lumen decreases monotonically from the lead receiving opening to the midpoint and from the midpoint to the end stop.

3. The electrical stimulation system of claim 1, wherein the lead lumen has an outer surface with a slope having a grade of at least 0.5%.

4. The electrical stimulation system of claim 1, wherein the width of the lead lumen continuously tapers along the longitudinal length of the lead lumen from the lead receiving opening to the end stop.

5. The electrical stimulation system of claim 1, wherein the width of the lead lumen decreases uniformly along the longitudinal length of the lead lumen from the lead receiving opening to the end stop.

6. The electrical stimulation system of claim 1, wherein the width of the lead lumen decreases in discrete steps along the longitudinal length of the lead lumen from the lead receiving opening to the end stop.

7. The electrical stimulation system of claim 1, wherein the width of the lead lumen decreases incrementally along the longitudinal length of the lead lumen from the lead receiving opening to the end stop.

8. The electrical stimulation system of claim 1, wherein each of the contacts defines a portion of the lead lumen.

9. The electrical stimulation system of claim 1, wherein each of the contacts has an inner diameter that is different than an inner diameter of at least another one of the contacts.

10. The electrical stimulation system of claim 1, wherein at least one of the contacts has an inner diameter that tapers from a larger inner diameter at one end of the at least one contact to smaller inner diameter at another end of the at least one contact.

11. The electrical stimulation system of claim 1, wherein a first one of the contacts has an inner diameter that exceeds an inner diameter of a second one of the contacts, wherein the first one of the contacts is nearer the lead receiving opening than the second one of the contacts.

12. The electrical stimulation system of claim 1, wherein the contact nearest the end stop has an inner diameter that is smaller than an inner diameter of each of the other contacts.

13. The electrical stimulation system of claim 1, wherein the width of the proximal end portion of the lead body has a grade of at least 0.5%.

14. The electrical stimulation system of claim 1, wherein the width of the proximal end portion of the lead body continuously tapers toward the proximal tip.

15. The electrical stimulation system of claim 1, wherein the width of the proximal end portion of the lead body increases uniformly from the proximal tip.

16. The electrical stimulation system of claim 1, wherein each of the terminals that is distal to a most proximal one of the terminals has a width that exceeds a width of the most proximal one of the terminals.

17. An electrical stimulation lead, comprising:
a lead body comprising a longitudinal surface, a distal end portion, a proximal end portion, a proximal tip, and a longitudinal length, wherein the proximal end portion is configured and arranged for insertion into an electrical stimulation lead connector and has a non-uniform width that monotonically increases from the proximal tip;
a plurality of terminals disposed along the proximal end portion of the lead body, wherein each of the terminals is configured and arranged to electrically couple to a corresponding one of a plurality of contacts of the electrical stimulation lead connector when the proximal end portion of the lead body is inserted into a lead lumen of a connector housing of the electrical stimulation lead connector;
a plurality of electrodes disposed along the distal end portion of the lead body; and
a plurality of conductors electrically coupling the terminals to the electrodes.

18. The electrical stimulation lead of claim 17, wherein the width of the proximal end portion of the lead body has a grade of at least 0.5%.

19. The electrical stimulation lead of claim 17, wherein the width of the proximal end portion of the lead body continuously tapers toward the proximal tip.

20. The electrical stimulation lead of claim 17, wherein each of the terminals that is distal to a most proximal one of the terminals has a width that exceeds a width of the most proximal one of the terminals.

* * * * *